(12) United States Patent
Dörr et al.

(10) Patent No.: US 11,417,473 B2
(45) Date of Patent: Aug. 16, 2022

(54) ELECTRODE ELEMENT FOR AN ENERGY STORAGE UNIT, ENERGY STORAGE UNIT, AND METHOD FOR PRODUCING ELECTRODE ELEMENT

(71) Applicant: BOTRONIK SE & Co. KG, Berlin (DE)

(72) Inventors: Thomas Dörr, Berlin (DE); Ingo Weiss, Berlin (DE)

(73) Assignee: BIOTRONIK SE & CO. KG

( * ) Notice: Subject to any disclaimer, the term of this patent is extended or adjusted under 35 U.S.C. 154(b) by 0 days.

(21) Appl. No.: 16/816,499

(22) Filed: Mar. 12, 2020

(65) Prior Publication Data

US 2020/0294725 A1 Sep. 17, 2020

(30) Foreign Application Priority Data

Mar. 15, 2019 (DE) ...................... 10 2019 106 677.8

(51) Int. Cl.
*H01G 9/048* (2006.01)
*H01G 9/00* (2006.01)
*H01G 9/042* (2006.01)

(52) U.S. Cl.
CPC ........... *H01G 9/048* (2013.01); *H01G 9/0029* (2013.01); *H01G 9/042* (2013.01)

(58) Field of Classification Search
CPC ........ H01G 9/008; H01G 9/012; H01G 9/045; H01G 9/048
See application file for complete search history.

(56) References Cited

U.S. PATENT DOCUMENTS

| 5,949,639 | A |   | 9/1999 | Maeda et al. |
| 5,968,210 | A | * | 10/1999 | Strange .................. H01G 9/055 29/25.03 |
| 6,025,095 | A |   | 2/2000 | Kawamura |
| 6,094,337 | A |   | 7/2000 | Ueda et al. |
| 6,310,527 | B1 |   | 10/2001 | Sugawara et al. |

(Continued)

FOREIGN PATENT DOCUMENTS

| DE | 69719911 B1 | 9/2003 |
| DE | 102011089174 A1 | 6/2013 |

(Continued)

OTHER PUBLICATIONS

European Search Report, dated Dec. 17, 2020, Appln. No. 20162671.0-1202.

(Continued)

*Primary Examiner* — Eric W Thomas
(74) *Attorney, Agent, or Firm* — Craig A. Fieschko, Esq.; DeWitt LLP

(57) ABSTRACT

An electrode element (1) for an energy storage unit (200), such as a capacitor, has an electrode body (100) made of an active electrode material (E), wherein the electrode body (100) includes one or more of: at least one cavity (110) on its surface or in its interior; at least one partial volume (120) of lower density; and/or a surface coating (D) covering at least a portion of the surface of the electrode body (100), such that the surface area covered by the surface coating (D) remains unwetted when in contact with an electrolyte. Energy storage units (200) incorporating the electrode element (1) are particularly suitable for use in implantable electrotherapeutic devices.

11 Claims, 9 Drawing Sheets

(56) References Cited

U.S. PATENT DOCUMENTS

| | | | |
|---|---|---|---|
| 6,416,559 | B1 | 7/2002 | Matsumura et al. |
| 6,421,226 | B1 | 7/2002 | O'Phelan et al. |
| 7,154,742 | B1 * | 12/2006 | Hahn ............... H01G 9/048 |
| | | | 361/528 |
| 9,502,179 | B2 * | 11/2016 | Ohchi ............... H01G 4/18 |
| 9,680,140 | B2 | 6/2017 | Tenzer |
| 2001/0004314 | A1 | 6/2001 | Copetti et al. |
| 2013/0155580 | A1 * | 6/2013 | Karnik ............ H01G 9/0029 |
| | | | 361/508 |
| 2013/0242467 | A1 * | 9/2013 | Biler ............... C09D 5/4476 |
| | | | 361/504 |
| 2013/0329335 | A1 * | 12/2013 | Obata ............. H05K 5/0217 |
| | | | 361/278 |
| 2014/0377604 | A1 | 12/2014 | Tenzer |
| 2016/0013469 | A1 | 1/2016 | Tajima et al. |
| 2017/0263933 | A1 | 9/2017 | Akikusa et al. |

FOREIGN PATENT DOCUMENTS

| | | | |
|---|---|---|---|
| DE | 102018203033 | A1 | 9/2019 |
| EP | 0926932 | A2 | 6/1999 |
| EP | 1111694 | A2 | 6/2001 |
| EP | 3193392 | A1 | 7/2017 |
| JP | H04127512 | A | 4/1992 |
| JP | 2001284166 | A | 10/2001 |

OTHER PUBLICATIONS

European Search Report, dated Aug. 11, 2020, Appln. No. 20162671.0-1202.
DE Search Report, dated Oct. 24, 2019.

* cited by examiner

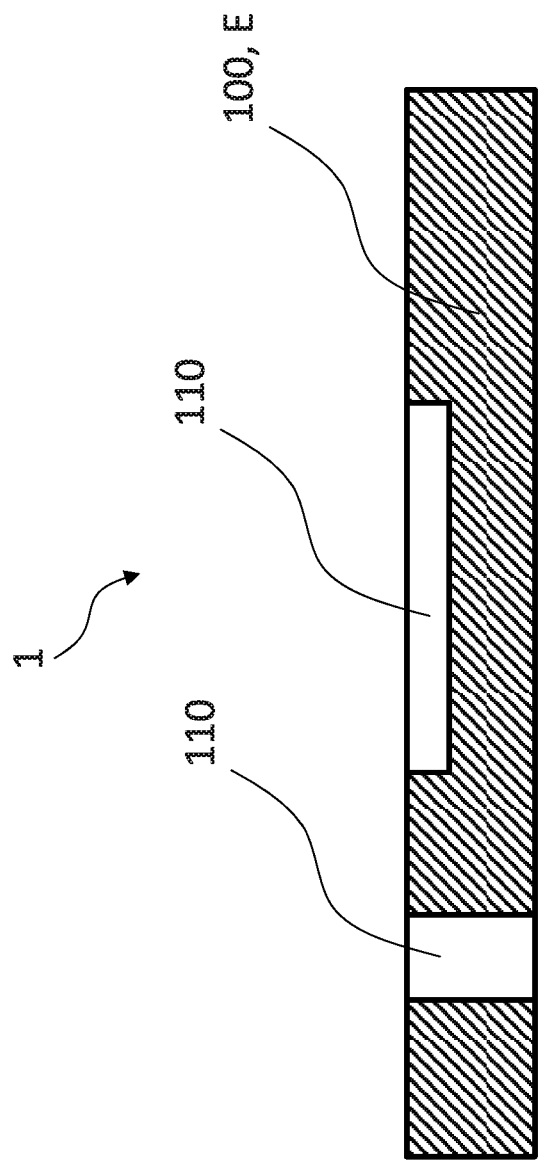

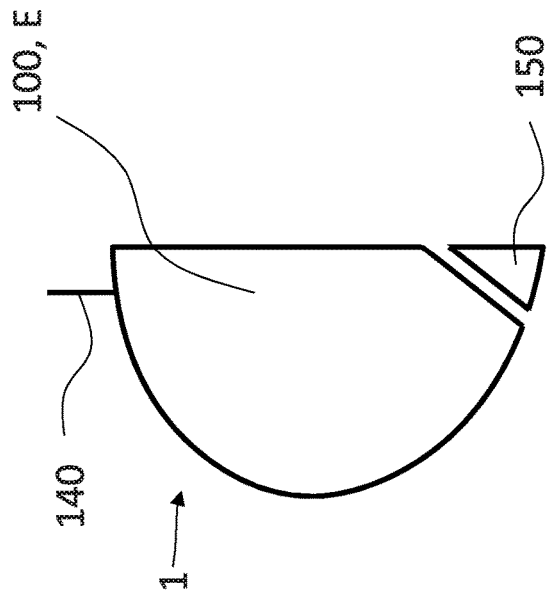
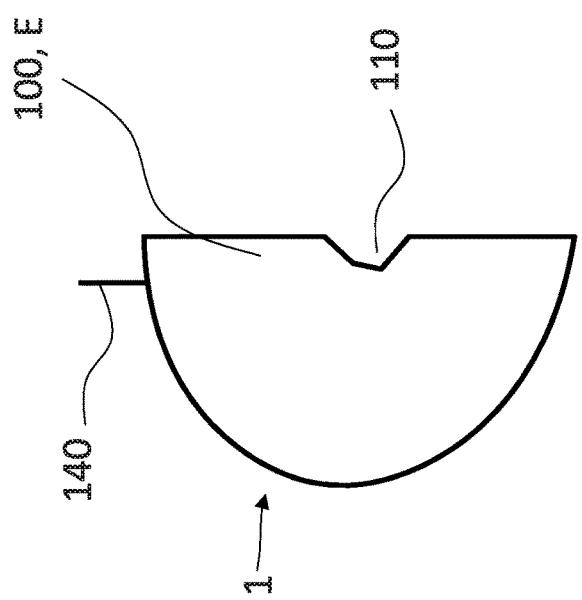
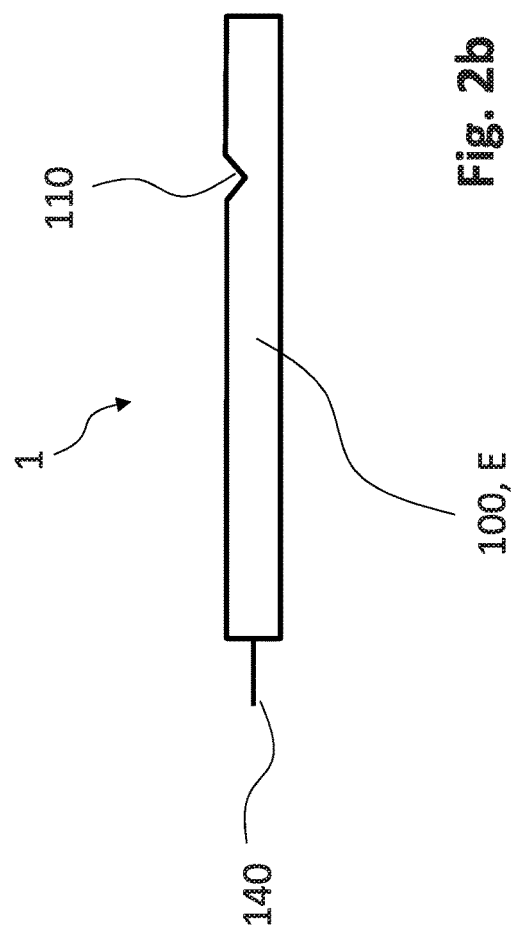

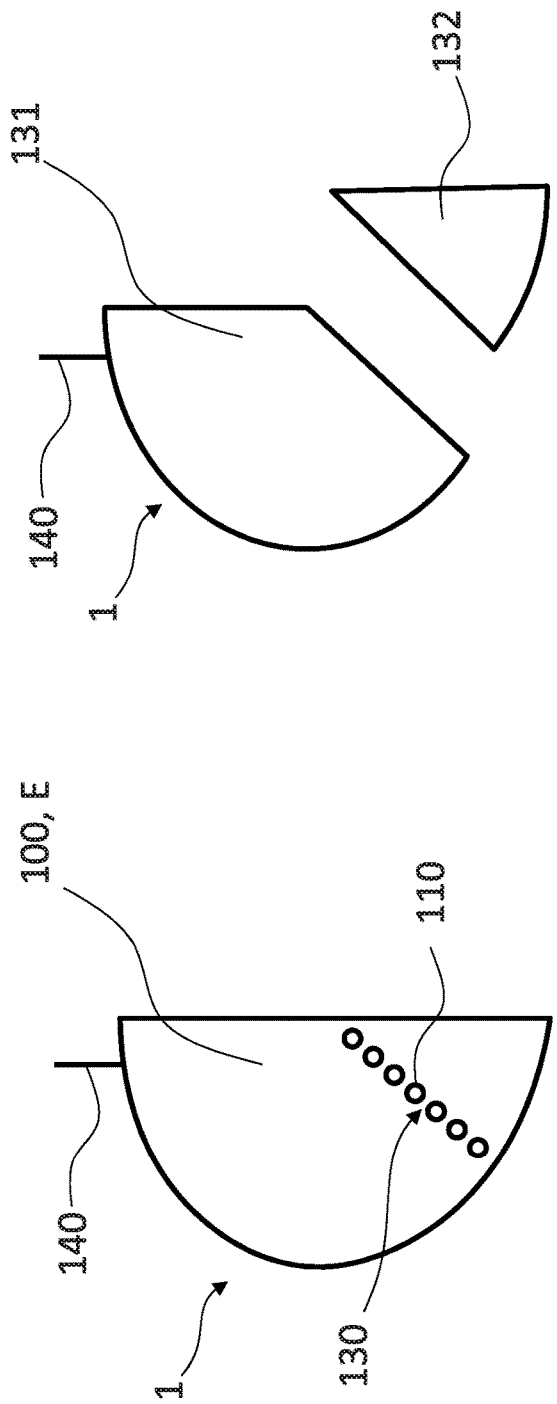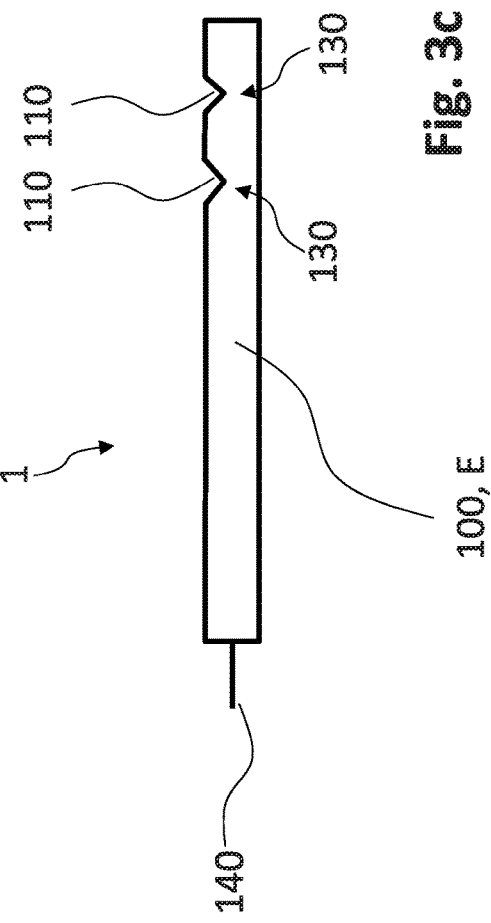

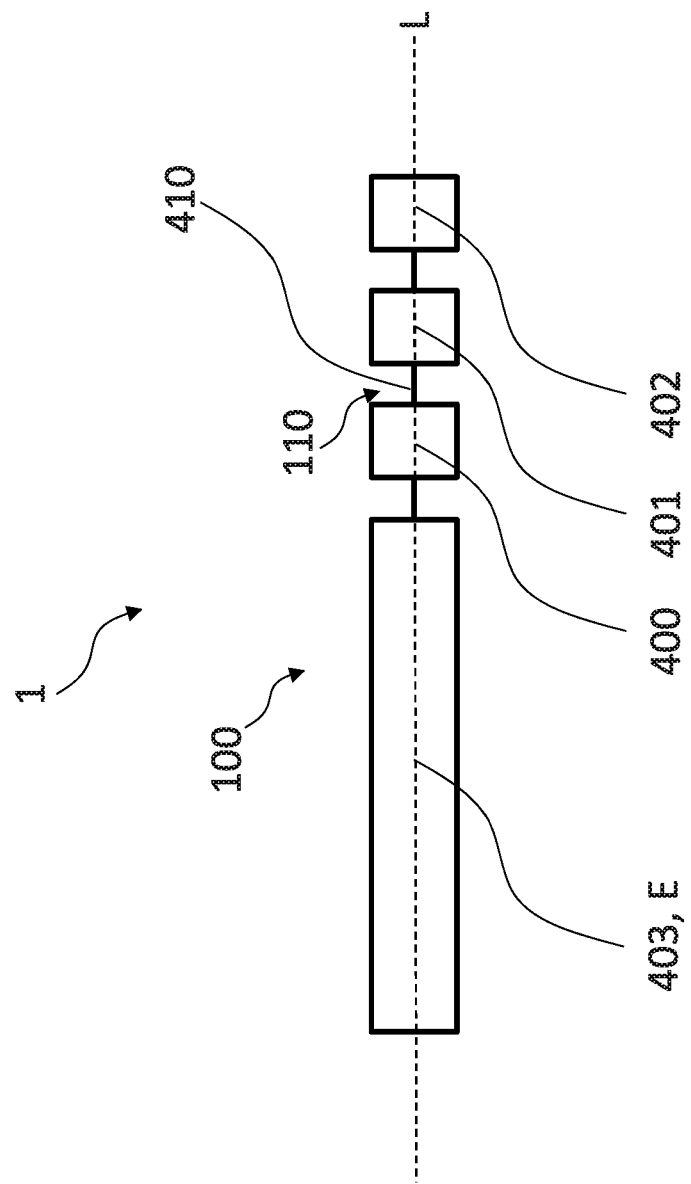

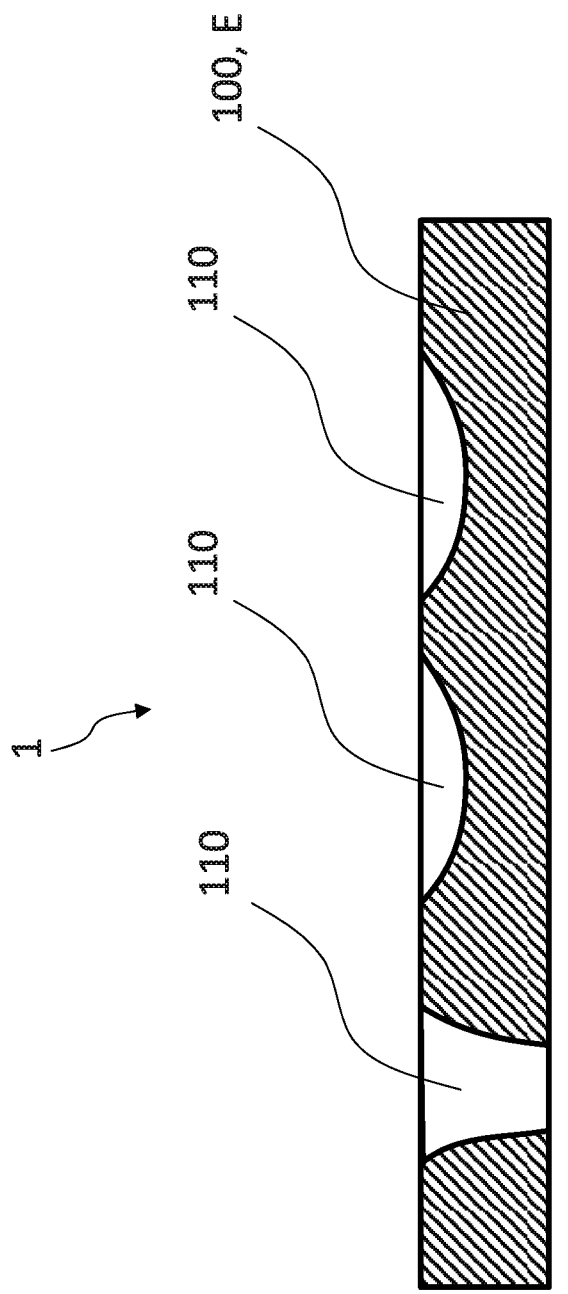

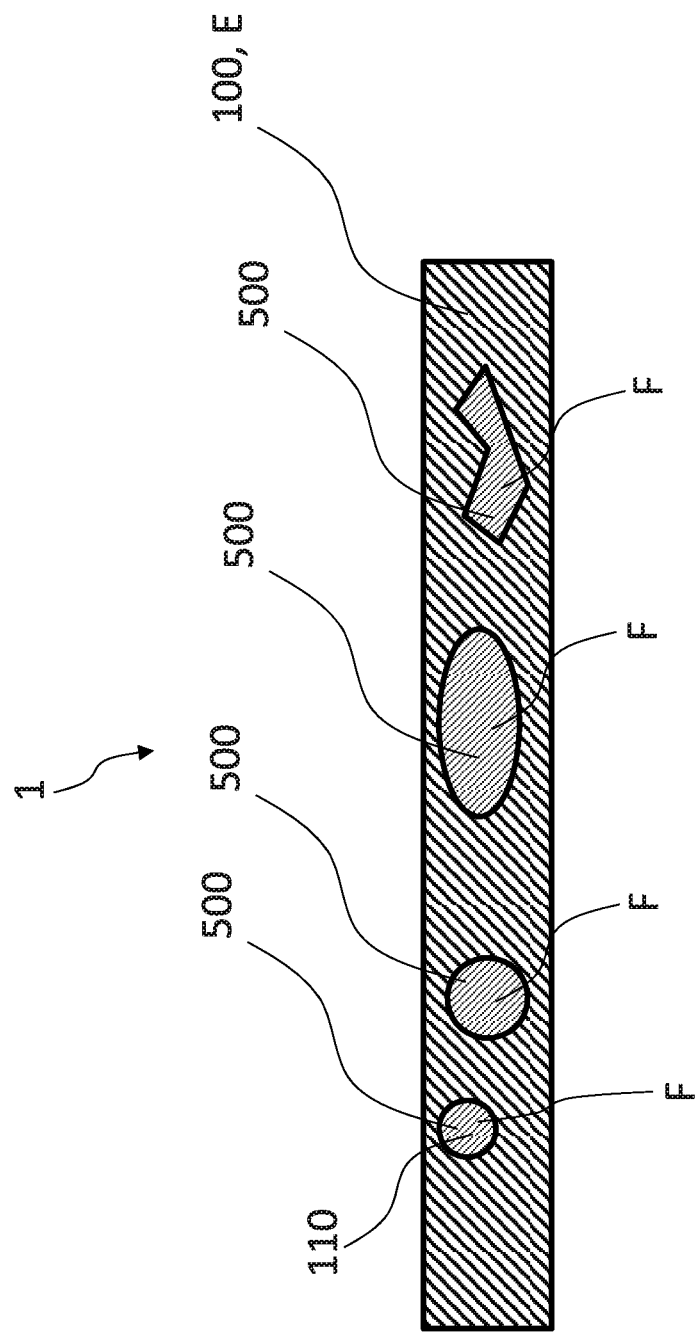

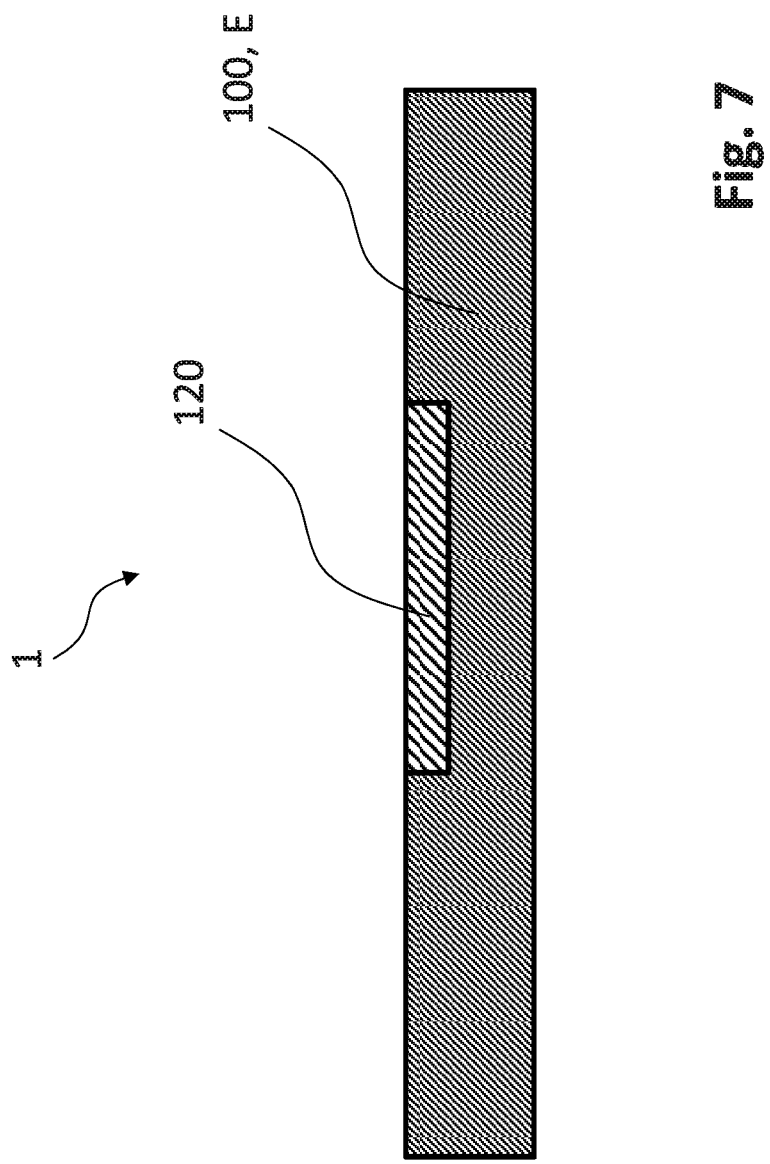

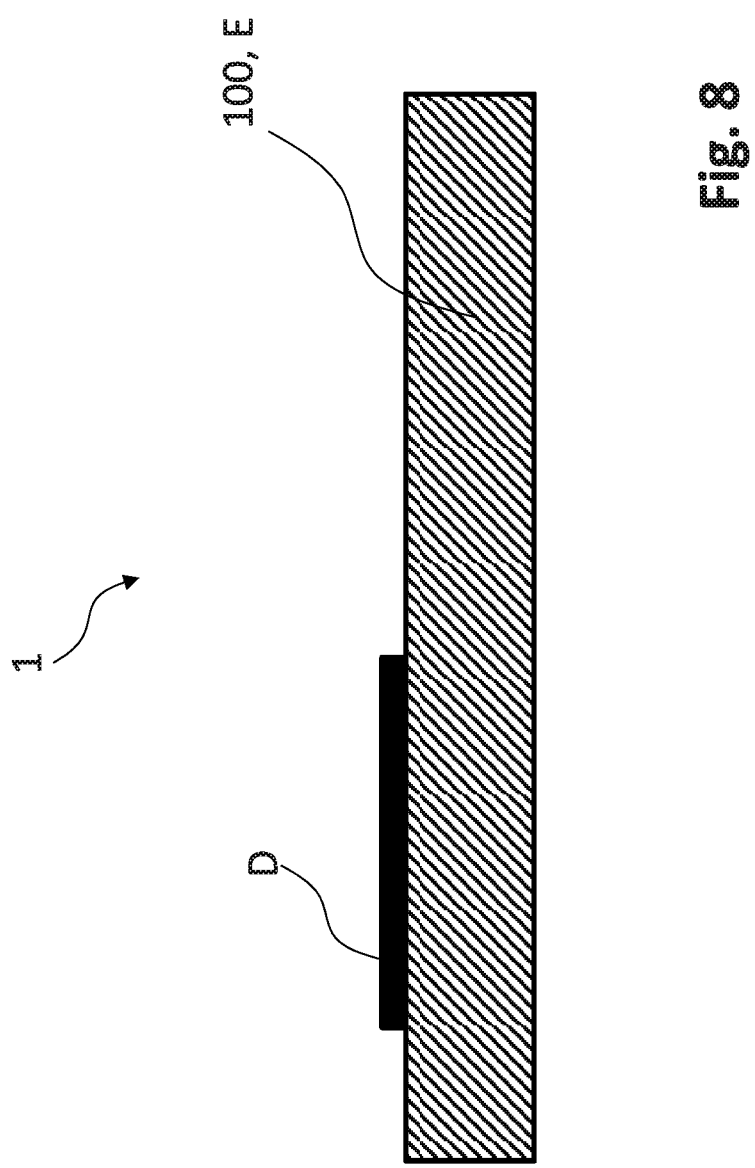

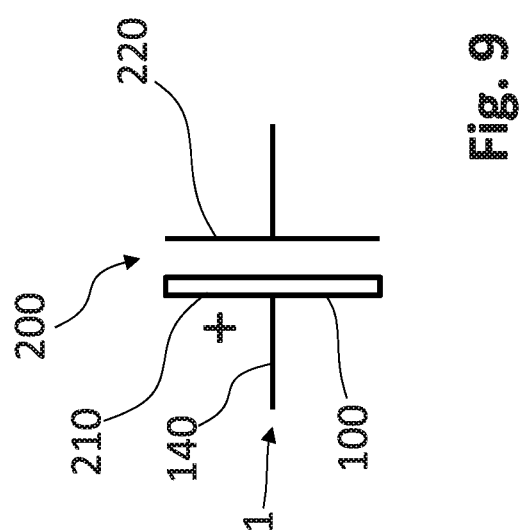

ELECTRODE ELEMENT FOR AN ENERGY STORAGE UNIT, ENERGY STORAGE UNIT, AND METHOD FOR PRODUCING ELECTRODE ELEMENT

FIELD OF THE INVENTION

The invention relates to an electrode element for an energy storage unit, in particular for use in an implantable electrotherapeutic device; to a method for producing an electrode element; to an energy storage unit, in particular for use in an implantable electrotherapeutic device; and to an implantable electrotherapeutic device, in particular an impulse generator such as, for example, a cardiac pacemaker, an implantable cardioverter-defibrillator, or a neurostimulator.

BACKGROUND OF THE INVENTION

Suitable energy storage units for implantable electrotherapeutic devices include batteries, e.g., lithium batteries and lithium ion batteries, and/or capacitors, e.g. electrolytic capacitors. Such energy storage units include electrodes having an electrode body made of an active electrode material.

For example, document DE 10 2011 089 174 A1 describes a battery anode component having least two spatially separated recesses serving as lithium receiving chambers. The recesses are separated from one another by a current collector component having a predetermined breaking point, whereby only very little lithium is released if the current collector component ruptures.

However, in prior energy storage unit production methods, fluctuations in the quality of the raw electrode materials used, and process fluctuations during production of the electrodes, can cause signification variation in the activity of the manufactured electrodes, and thus in the storage capacity of the energy storage units in which the electrodes are installed.

In order to provide the required energy storage capacity within a prespecified tolerance, the raw electrode materials are selected, and if necessary the configuration of the active electrode material of the electrode bodies may be varied. This has the disadvantage that the electrode design is generally made experimentally, and the tested electrodes may be unusable in end products, leading to higher production costs. If electrode configuration is altered to attain a desired energy density, the electrode's external dimensions may vary enough that component fit during assembly of the energy storage unit is no longer accurate. Likewise, in order to attain a prespecified energy density with a modified configuration, the manufacturing and assembly tools and processes may require modification. The production and modification of such tools is very expensive, particularly as modification may require overall tool redesign.

SUMMARY OF THE INVENTION

The invention provides an electrode element for an energy storage unit; a method for producing an electrode element; an energy storage unit; and an implantable electrotherapeutic device using the energy storage unit, all of which are improved with respect to the aforementioned drawbacks. In particular, the invention seeks to provide an energy storage unit having lesser production-related fluctuations in its storage capacity, and which can be produced in a cost-effective manner.

A first aspect of the invention relates to an electrode element for an energy storage unit, particularly a capacitor, wherein the electrode element has an electrode body that is formed from active electrode material, and wherein:

(1) the electrode body includes at least one cavity on its surface or in its interior, wherein the mass of the electrode body is adjusted, in particular to a desired value, by the cavity; and/or (2) the electrode body includes at least one partial volume of lower density, wherein the active electrode material has a lower density within the partial volume than outside of the partial volume, whereby the mass of the electrode body is adjusted, in particular to a desired value, by the partial volume of lower density; and/or (3) the electrode body includes a surface coating, e.g. an impregnating agent such as silicone (adhesive), epoxy resin, polymers, or varnish, wherein the surface coating covers at least a portion of the surface of the electrode body, and wherein the surface coating is designed such that the surface of the electrode body covered by the surface coating remains unwetted when in contact with an electrolyte.

The electrode element preferably includes a terminal lead electrically connected to the electrode body.

The mass (and thus the electrode activity) of the active electrode material is reduced by the cavity or cavities, and/or by the partial volume(s), compared to an electrode element lacking the cavity/cavities and/or partial volume(s). Likewise, the accessible active surface of the electrode body may be reduced in a controlled manner using the surface coating.

By these arrangements, when the electrode element is used in an energy storage unit, the storage capacity of the energy storage unit may advantageously be simply and accurately adjusted, since this storage capacity is a function of the mass of the electrode body and/or of its surface area that can be wetted by an electrolyte. This makes it possible to compensate for fluctuations in the properties of the raw electrode materials used, and/or for fluctuations in manufacturing parameters. Thus, complex tests required in prior production methods, and expensive tool redesign or replacement, are unnecessary, and energy storage units with low storage capacity tolerances can be produced with less expense.

Throughout this document, "electrode element" refers to a component suitable for use as an electrode, in particular an anode, in an energy storage unit such as a capacitor, in particular an electrolytic capacitor. The electrode includes a unitary electrode body having any desired shape and is made of an active electrode material, but may have additional components (e.g. a surface coating and/or filler material) in addition to the electrode body.

"Active electrode material" refers to a material that is configured to release or receive charge carriers (e.g., electrons or ions) in an energy storage unit such as a capacitor. The active electrode material preferably includes or essentially consists of a valve metal, in particular aluminum, tantalum, niobium, or zirconium. The term "valve metal" refers to a metal that, through anodic oxidation, forms a coating of metal oxide that is electrically non-conducting. Such valve metals may be used for electrodes, e.g., anodes of electrolytic capacitors, wherein the metal oxide coating functions as dielectric material.

Depending on the material properties of the active electrode material, the mass of the active electrode material, and the shape of the electrode body, the electrode element has a certain activity, i.e., a specific tendency to receive or release charge carriers. The higher this activity, the greater the storage capacity of an energy storage unit in which the electrode element is used as electrode, in particular as an anode.

In versions of the electrode element having the aforementioned cavity, the cavity may be defined by a depression or blind hole in the electrode body, by through-hole extending through the electrode body, or by a hollow chamber within the interior of the electrode body. The cavity may have any shape, e.g. it may have a polygonal, round, or oval-shaped cross-section. Cavities of different shapes and sizes may also be combined with one another, e.g., an electrode body may include some or all of blind holes, through-holes, and interior chambers. The cavity or cavities may be added to the electrode body in a controlled manner during the electrode body's production process. Adding cavities allows the activity of the electrode element to be adjusted in a particularly simple and variable manner.

In versions of the electrode element having the aforementioned partial volumes of lower density, partial volumes may likewise be disposed on the surface of, or within the interior of, the electrode body. The lower density of the partial volume may be attained, for example, using active electrode material having higher porosity within this partial volume. For example, the electrode body may be shaped by pressing powdered raw electrode material, wherein the partial volume(s) are appropriately formed by application of lesser pressure, resulting in correspondingly higher porosity. Porosity variation can depend on the properties of the raw electrode material, for example, the grain size of the powder that is used as raw material.

In versions of the electrode element having the aforementioned surface coating, the electrode body may have capillaries or other cavities so that one or more portions of the electrode body have a porous structure, with the surface coating being configured such that the surface coating is drawn into the capillaries of the electrode body after application to the electrode body. In particular, the viscosity of the surface coating may be chosen such that the coating is drawn into the capillaries of the electrode body after being applied to the electrode body. The surface coating remains in or on the electrode body when hardened, such that it immovably remains in place.

The surface coating prevents an electrolyte, in particular a liquid electrolyte, from wetting the region of the electrolyte body covered by the surface coating. Thus, the coated region of the active electrode material is functionally deactivated. The dosing (amount/thickness) of the surface coating determines the extent of deactivation, and thus the effect on the activity of the active electrode material. Adjusting the dosing of the surface coating to advantageously allows adjustment of the deactivation (and conversely the activity) of the electrode element.

In some versions of the invention, the cavity or the partial volume of lower density form a separation boundary designed such that the electrode body may be broken, cut, or otherwise mechanically separated at the separation boundary into separate body segments. The separation boundary is designed as a predetermined mechanical separation boundary, wherein the electrode body may be mechanically separated at the target breaking point by breaking, cutting, or otherwise separating the electrode body into a first body segment and a second body segment. The mechanical separation effects the controlled reduction in the mass of the active electrode material. Following separation, the first body segment and/or the second body segment may be used as separate electrode elements, e.g., in an energy storage unit. This has the advantage that, even after the conclusion of the essential production steps for the electrode element, its activity may be adjusted in a simple and easily controlled manner, e.g., during assembly of an energy storage unit. The separation boundary may be formed by a cavity, e.g. a notch or channel in the surface of the electrode body, or by a region of lower density in the active electrode material, or by a hollow chamber filled with a filler material having a lower density than the active electrode element. The separation boundary may be defined by multiple such cavities, regions, or chambers, as by arranging them along a path along which the electrode element is to be broken or otherwise separated.

In another version, the electrode body includes a first partial body, a second partial body, and a connecting element, all made of the active electrode material, wherein the first partial body and the second partial body are mechanically connected to one another by the connecting element. The connecting element extends along a longitudinal axis between first partial body and the second partial body, and has a smaller cross-sectional area perpendicular to the longitudinal axis than the first partial body and the second partial body, thereby forming a cavity between the partial bodies and the connecting element. The first partial body and the second partial body may be mechanically separated by severing the connecting element, whereby the connecting element serves as a separation boundary. Severing the connecting element effects controlled reduction in the mass of the active electrode material. Thus, once essential production steps are completed, the activity of the electrode element may be simply reduced, e.g., during the assembly of an energy storage unit. The partial bodies and the connecting element include or essentially consist of the same active electrode material, e.g., a valve metal. The electrode element is particularly suited for use as an electrode in an electrolytic capacitor. The connecting elements may be wires or other linking structures made of the active electrode material.

The electrode body may include multiple partial bodies and connecting elements, wherein each pair of partial bodies is mechanically connected by a connecting element, and wherein the connecting elements have smaller cross-sectional areas than their adjacent partial bodies, whereby cavities are formed between the partial bodies adjacent their connecting elements. The partial bodies may be mechanically separated by severing the connecting elements therebetween. In such electrode bodies, the partial bodies may be connected in a linear chain-like manner by the connecting elements, or branches may be provided so that a two or three-dimensional arrangement of partial bodies results.

In another version, the electrode element includes a filler material, such as ceramic or glass, within the cavity or cavities of the electrode body. The filler material may be in the interior of the electrode body, and may be particles having spherical or other shapes with diameters of 0.1 μm to 3 mm, preferably 0.1-50 μm or 100-1000 μm. More generally, the particles may have a mean diameter or mean grain size in the order of magnitude of the powder size of the raw material of the active electrode material. Typically, a raw material powder having a mean grain size of less than 0.6 mm is used, preferably in the range of 75 μm to 150 μm. The term "mean diameter" or "mean grain size" refers to the arithmetic mean of all diameters of the particles, or to the median of the size distribution of all particles.

Another aspect of the invention relates to a method for manufacturing an electrode element for an energy storage unit, wherein an electrode body is formed of an active electrode material, in particular in a shaping step, and wherein:

(1) the mass of the active electrode material of the electrode body is reduced, and/or
(2) a surface coating is applied to cover at least a portion of the surface area of the electrode body, so that the surface area of the electrode body covered by the surface coating remains unwetted when in contact with an electrolyte.

"Shaping step" refers to any production step wherein the electrode body receives its shape. A shaping step may be, for example, a metal casting method, a sintering method, a punch method, or a cutting method. The manufacturing method may further include the step of electrically connecting the active electrode material to a terminal lead.

When the manufacturing method includes the step of reducing the mass of the electrode body (as by adding a cavity to the electrode body, and/or by providing a partial volume having reduced density), the activity of the electrode element may advantageously be adjusted such that an energy storage unit using the electrode element as an electrode has a desired storage capacity. The activity of the electrode element may be adjusted during production, as by machining out a defined volume in order to adjust the mass of the electrode body, and/or by providing one or more cavities to define a separation boundary such that the activity of the electrode element may be adjusted by separating the electrode body at the separation boundary.

When the manufacturing method includes the step of providing a surface coating on the surface of the electrode body, the surface coating prevents electrolyte from wetting the region of the electrode material covered by the surface coating, functionally deactivating the active electrode material at this region. The dosing of the surface coating determines the extent of deactivation. To perform this step, an initially liquid impregnating agent or other surface coating is applied to at least a portion of the electrode body, which preferably has capillaries or other pores etched or otherwise formed therein, or otherwise has a permeable structure. When the surface coating is applied to the electrode body, the surface coating is drawn into the pores. The surface coating preferably has a viscosity and/or other properties such that it is drawn into the pores of the electrode body after being applied thereon. If the electrode body is made of a valve metal, the surface coating is applied after the formation of the nonconducting metal oxide coating of the valve metal. The surface coating hardens after it enters the pores, such that it thereafter remains in place on and within the electrode body.

In the shaping step, the electrode body may be shaped by pressing and sintering powdered raw material (with or without binding agent). Alternatively or additionally, the electrode body may be shaped by punching and/or cutting (e.g., by means of laser, water jet, electron beam, or sawing).

When the manufacturing method includes the step of reducing the mass of the electrode body by forming a cavity upon or within the electrode body, formation of the cavity reduces the mass of the active electrode material. The cavity may be formed after formation of the electrode body, e.g., after the conclusion of the shaping step, by removing active electrode material from the electrode body. The active electrode material may be removed by drilling, milling, punching, or other methods. The formed cavity may be, for example, a blind hole or a through-hole.

The active electrode material may also or alternatively be removed by producing a notch or other cavity in the outer surface of the electrode body, or by separating a portion of the electrode body, as by sawing, grinding, or breaking.

Where the active electrode material is a valve metal, the cavity is preferably formed following formation of a metal oxide coating, which may occur by means of anodic oxidation of the valve metal. Preferably, following formation of the cavity, a metal oxide coating of the valve metal is formed within the cavity by anodic oxidation.

The cavity may be formed during the shaping step by displacing active electrode material during the formation of the electrode body. This can be done by pressing in cavities (e.g., blind holes or other depressions, or through-holes, preferably having rounded surfaces). The cavities are preferably formed such that the nominal outer dimensions of the electrode body are retained. Pressing is preferably performed by means of a stamp, most preferably an adjustable stamp.

The electrode body is also preferably performed by pressing, wherein the pressing of the cavities is preferably accomplished simultaneously with the pressing of the electrode body.

In an exemplary manufacturing method, at least one partial volume of the electrode body is formed during the formation of the electrode body (e.g, during the shaping step), wherein the active electrode material has a lower density within the partial volume than outside of the partial volume.

In an alternative exemplary manufacturing method, one or more cavities formed in the electrode body, and/or one or more partial volumes of lower density, define a separation boundary within the electrode body, allowing mechanical separation of the electrode body at the separation boundary into a first body segment and a second body segment. The active electrode material is preferably a valve metal, wherein mechanical separation of the electrode body at the separation boundary into two or more body segments is done after formation of a metal oxide coating of the valve metal. After such separation, a metal oxide coating is again preferably formed on the body segments where separation occurred.

In another version of the manufacturing method, the electrode element includes two or more partial bodies, each being connected to at least one other partial body, or to the remainder of the electrode body, by a connecting element. The partial bodies and the connecting element are each made of the active electrode material. Each connecting element extends along a longitudinal axis, and has a smaller cross-sectional area perpendicular to the longitudinal axis than the first partial body and the second partial body, thereby defining a cavity at the connecting element between the portions of the electrode body joined by the connecting element. The connecting element defines a separation boundary whereby the electrode body may be mechanically separated by severing the connecting element, either during or after production of the electrode body. The connecting element may be defined by a wire or other link made of the active electrode material. The active electrode material is preferably a valve metal, wherein the connecting element is severed following formation of a metal oxide coating of the valve metal of the electrode body. Preferably, following such severing, a metal oxide coating of the valve metal is formed at the severed location.

In versions of the manufacturing method wherein cavities are provided on or within the electrode body, the cavity or cavities may be filled with a filler material, for example, ceramic or glass. The filler material may stabilize the mechanical structure of the electrode body. If the electrode element is used as an electrode in an electrolytic or other capacitor, the filler material is preferably chosen such that it does not negatively impact the functioning of the capacitor. The filler material is preferably added to the electrode body during or after the shaping step in which the electrode body is formed, and may be accomplished by pressing the filler material into the electrode body. The filler material may be particles having spherical shapes with diameters of 0.1 μm to 3 mm, preferably 0.1-50 μm or 100-1000 μm. More generally, the particles may have a mean diameter or mean grain size in the order of magnitude of the powder size of the raw material of the active electrode material. Typically, a raw material powder having a mean grain size of less than 0.6 mm is used, preferably in the range of 75 μm to 150 μm.

During manufacture, the activity of the electrode element may be measured, and thereafter the cavity and/or the partial volume of lower density may be formed, and/or the surface coating may be applied, such that the activity of the electrode element is adjusted to a target value. The adjustment may be controlled by remeasuring the activity after formation of the cavity and/or the partial volume of lower density, and/or after the application of the surface coating. The control measurement may be performed on a random sample of the produced electrode elements, that is, the calibration may be based on random samples and applied by lot. The activity of the electrode element may be measured by determining a storage capacity of an energy storage unit wherein the electrode element forms an electrode. Alternatively, activity measurement may be done indirectly, e.g., by determining the mass of the active electrode material.

Another aspect of the invention relates to an energy storage unit, in particular for use in an implantable electrotherapeutic device, wherein the energy storage unit has at least one electrode element as described above, and wherein the electrode element forms an electrode, in particular an anode, of the energy storage unit. The energy storage unit may be defined by a capacitor, in particular an electrolytic capacitor.

Another aspect of the invention relates to a method for manufacturing an energy storage unit wherein the energy storage unit includes an electrode element as described above, wherein the electrode element forms an electrode, preferably an anode, of the energy storage unit, and wherein a storage capacity of the energy storage unit is adjusted or calibrated by reducing the mass of the active electrode material of the electrode body, and/or or by applying the surface coating to the electrode body of the electrode element. Adjustment of the storage capacity of the energy storage unit preferably occurs by less than 20%, in particular by less than 5%.

Another aspect of the invention relates to an implantable electrotherapeutic device, in particular an impulse generator, wherein the implantable electrotherapeutic device includes at least one energy storage unit as described above. The energy storage unit acts as an energy source for operating the implantable electrotherapeutic device. The impulse generator may be a cardiac pacemaker, an implantable cardioverter-defibrillator (ICD), or a neurostimulator.

BRIEF DESCRIPTION OF THE DRAWINGS

Referring to the accompanying drawings:

FIG. 1 depicts an exemplary electrode element having cavities in the electrode body;

FIGS. 2a-2c illustrate an exemplary version of the electrode element having a cavity, and schematically depict a method for adjusting electrode activity;

FIGS. 3a-3c illustrate another exemplary version of the electrode element having a separation boundary, and schematically depict another method for adjusting electrode activity;

FIG. 4 illustrates another version of the electrode element, having partial bodies and connecting elements;

FIG. 5 illustrates another exemplary version of the electrode element having cavities formed therein;

FIG. 6 illustrates another version of the electrode element having a filler material in the interior of the electrode body;

FIG. 7 illustrates another version of the electrode element having a partial volume of different density;

FIG. 8 illustrates another version of the electrode element having a surface coating;

FIG. 9 illustrates an exemplary version of an energy storage unit.

DETAILED DESCRIPTION OF EXEMPLARY VERSIONS OF THE INVENTION

Expanding on the foregoing discussion, FIG. 1 is a sectional illustration of an exemplary electrode element 1 having a unitary electrode body 100 made of an active electrode material E. In the exemplary version depicted, the electrode body 100 has two cavities 110 or cavities, wherein one of the cavities 110 is designed as a blind hole, that is, a cavity that does not go all the way through the body 100, and the other cavity 110 is embodied as a through-hole, that is, as a cavity that goes entirely through the body 100.

The cavity 110 allows the activity of the electrode element 1 to be adjusted to a desired value as early as during manufacture of the electrode body 100, by reducing the mass of the electrode body 100. The "activity" of the electrode element 1 means the tendency to receive or release charge carriers, this tendency leading to a specific storage capacity of an energy storage unit (such as a capacitor) if the electrode element 1 is used as an electrode, in particular as an anode. This activity is in particular a function of the mass of the electrode body 100, or of the surface area of the electrode body 100 accessible to an electrolyte.

FIGS. 2a-2c depict another exemplary implementation of the electrode element 1, wherein the electrode element 1 includes an electrode body 100 and a conductively connected connecting pin 140 to which electrical connections can be made. FIG. 2a depicts a top view of the electrode element 1. The electrode body 100, which is made of the active electrode material E, has an essentially semi-circular shape, wherein a roughly semi-circular cavity 110 has been formed in the straight side of the semi-circle. FIG. 2b is a sectional view of an electrode element 1 shaped as in FIG. 2a.

FIG. 2c provides a schematic depiction of a manufacturing method for the electrode element 1. In this method, first the semi-circular electrode body 100 is made from the active electrode material E and connected to the connecting pin 140. Thereafter, an electrode piece 150 is separated from the electrode body 100, for example by cutting, sawing, or milling. In this way, the mass of the active electrode material E is reduced in a controlled manner in order to obtain an appropriate desired electrode activity when the electrode element 1 is used in an energy storage unit. In this version of the manufacturing method, no cavity 110 is made in the electrode body 100.

FIG. 3 depicts another exemplary version of the electrode element 1 in a top view (FIGS. 3a and 3b) and in section (FIG. 3c). FIG. 3a depicts the electrode element 1 prior to a separating process, and FIG. 3b depicts the electrode element 1 following the separating process. The electrode element 1 has an essentially semicircular shape and includes a unitary electrode body 100 made of an active electrode material E, and a connecting pin 140. The electrode body 100 furthermore has cavities 110 arranged along a linear path, and which may be formed as through-holes or as blind holes. Together the cavities 110 form a separation boundary or predetermined breaking point 130 that makes it possible to break or otherwise mechanically separate the electrode body 100 at the separation boundary 130 into a first body segment 131 and a second body segment 132. FIG. 3b depicts the first body segment 131 and the second body segment 132 following separation at the separation boundary 130.

FIG. 3c depicts an exemplary electrode element 1 in section, wherein the separation boundaries or predetermined breaking points 130 are defined by cavities 110 in the form of notches. After completion of the essential production steps for the electrode element 1, the mass of the electrode body 100 may be reduced by separating at the separation boundary 130 in order to adjust the activity of the electrode element 1 to a desired value, e.g., in order to calibrate the storage capacity of an energy storage unit in which the electrode element 1 is used as an electrode (in particular an anode). One of the body segments 131 and 132 may then further be used as an electrode element 1 having reduced mass and activity, here preferably the first body segment 131, which bears the connecting pin 140.

FIG. 4 depicts a sectional view of an exemplary version of the electrode element 1, which in this case has already been produced with body segments 400, 401, 402, 403 made of the active electrode material E. The body segments 400, 401, 402, 403 are connected to one another via connecting elements 410 made of the same active electrode material E (for example, a valve metal) as the body segments 400, 401, 402, 403. The body segments 400, 401, 402, 403 are connected to one another as a linear chain via the connecting elements 410, with the connecting elements 410 extending along a common longitudinal axis L. However, it is also possible to create branched structures or a two or three-dimensional arrangement of body segments of the electrode body 100.

The body segments 400, 401, 402, 403 may be broken, cut, or otherwise mechanically separated from one another at the connecting elements 410. This advantageously allows reduction of the mass of the electrode body 100 in a controlled and simple manner even after the essential production steps for the electrode element are finished, and thereby allows adjustment of the electrode activity of the electrode element 1, e.g., when used in an energy storage unit, wherein the electrode activity influences the energy storage unit's storage capacity.

The connecting elements 410 may be formed as wires or other linking structures bridging the body segments 400, 401, 402, 403. The connecting elements 410 have a smaller cross-sectional area perpendicular to the longitudinal axis L than the body segments 400, 401, 402, 403, whereby a cavity 110 is created between body segments 400, 401, 402, 403 at each connecting element 410. The connecting elements 410 thereby define separation boundaries between body segments 400, 401, 402, 403.

FIG. 5 depicts a section through an electrode body 100 of an exemplary electrode element 1 having cavities 110 defined therein. One of these cavities 110 is defined as a through-hole, while the other two cavities 110 are designed as depressions (blind holes) in the surface of the electrode body 100. Such cavities 110 may be formed during a shaping step in the production of the electrode body 100, e.g., by pressing into the electrode body 100 by means of a stamp.

By selecting the dimensions of the cavities, the mass of the active electrode material E is adjusted to a desired value in order to attain a desired activity regardless of variation in the raw electrode materials and previous production steps. This activity then assists in providing the desired storage capacity of an energy storage unit incorporating the electrode element 1.

FIG. 6 is a sectional depiction of an exemplary electrode element 1 having cavities 110 within the interior of the electrode body 100. These cavities 110 are filled with a filler material F, as depicted at reference numeral 500. This filler material F differs from the active electrode material E, and in particular does not have any active electrode properties. The filler 500 may be pressed into the electrode body 100, for example, during a shaping step for the electrode body 100. The volume of the filler 500 may be shaped, sized, and positioned as appropriate for the materials and configuration of a given electrode body 100. The filler 500 may have a particulate, liquid, or other form which accommodates the shape of the cavities 110 when poured or injected therein.

The filler material F of the filler 500 allows the mass of the active electrode material E, and thus the activity of the electrode element 1, to advantageously be adjusted to a desired value, since the active electrode material E of the cavities is replaced by the filler material F. At the same time, the mechanical stability of the electrode body 100 is increased due to use of the filler material F in the cavities 110 in place of empty voids.

FIG. 7 is a sectional depiction of another exemplary electrode element 1 wherein the surface of the electrode body 100 has a partial volume 120 therein of lower density. The electrode body 100 has the same active electrode material E both within and outside the partial volume 120, but the density of the active electrode material E within the partial volume 120 is lower than outside the partial volume 120.

The activity of the electrode element 1 is therefore reduced compared to an electrode element 1 having uniformly higher density, so that when the electrode element 1 is used as an electrode (especially as an anode) in an energy storage element, selection of the size and density of the partial volume 120 determines the element's storage capacity.

The partial volume 120 need not be disposed on the surface of the electrode body 100, but instead may be situated within the interior of the electrode body 100. Rather than being of lower density, one or more partial volumes may instead be of higher density to allow adaptation of the activity of the electrode element 1.

FIG. 8 depicts another exemplary electrode element 1 having an electrode body 100 made of the active electrode material E, and having a cover layer made of a surface coating D, for example an impregnating agent, on the surface of the electrode body 100. The surface coating D prevents wetting of the surface of the electrode body 100 with an electrolyte, thereby preventing the covered portion of the electrode body 100 from functioning as an electrode, in particular in an energy storage unit. The activity of the electrode element 1 is thereby reduced, depending on the size and configuration of the surface coating D on the electrode body 100. The surface coating D therefore allows adjustment of the storage capacity of an energy storage unit that uses the inventive electrode element 1.

As an alternative to the version of the electrode element 1 illustrated in FIG. 8, the surface coating D might cover pores or other cavities that run from the surface into the interior of the electrode body 100 (such cavities being unfilled, or alternatively having filler material therein).

FIG. 9 schematically depicts an version of an energy storage unit 200 that has anode 210 and cathode 220, wherein the energy storage unit 200 uses the electrode element 1 as an electrode, specifically as anode 210. The energy storage unit 200 is designed as an electrolytic capacitor. The electrode element 1 is made of a valve metal, such as aluminum, tantalum, niobium, or zirconium, with an oxide layer of this valve metal forming the dielectric material of the electrolytic capacitor.

The versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. An electrode element (1) for an electrolytic capacitor (200) having a liquid electrolyte, the electrode element including an electrode body (100) made of an active electrode material (E) selected from at least one of tantalum and niobium and a terminal lead electrically connected to the electrode body (100), wherein the electrode body (100) includes:
   a. a cavity (110) upon or within the electrode body (100), wherein the cavity (110) is configured to adapt electrode activity of the electrode body (100) to a predefined electrode activity;
   b. filler material (F) filling the cavity (110) of the electrode body (100), the filler material (F) having an electrode activity different from the electrode activity of the active electrode material (E).

2. The electrode element (1) of claim 1 wherein the cavity (110) defines a separation boundary (130), the separation boundary (130) being configured to ease mechanical separation of the electrode body (100) into a first body segment (131) and a second body segment (132) at the separation boundary (130).

3. The electrode element (1) of claim 2 wherein the cavity (110) extends along:
   a. an elongated path extending between edges of the electrode body (100), and
   b. a major portion of a distance between the edges of the electrode body (100).

4. The electrode element (1) of claim 1 wherein several of the cavity (110), the cavities (110) being separate from each other,
are arrayed in spaced relationship along a path extending between edges of the electrode body (100), the path defining a separation boundary (130) configured to ease mechanical separation of the electrode body (100) into a first body segment (131) and a second body segment (132) at the separation boundary (130).

5. The electrode element (1) of claim 1 defining an anode of the capacitor (200).

6. The electrode element (1) of claim 1 further including an implantable electrotherapeutic device having the capacitor (200) therein.

7. An electrode element (1) for an electrolytic capacitor (200) having a liquid electrolyte, the electrode element including an electrode body (100) made of an active electrode material (E) selected from at least one of tantalum and niobium and a terminal lead electrically connected to the electrode body (100), wherein:
   a. the electrode body (100) includes:
      (1) two or more partial bodies (400, 401) adjacently arrayed along a longitudinal axis (L),
      (2) one or more connecting elements (410), each connecting element (410) connecting the partial bodies (400, 401) of each pair of adjacent partial bodies (400, 401),
      (3) a cavity (110) upon or within the electrode body (100), wherein the cavity (110) is configured to adapt electrode activity of the electrode body (100) to a predefined electrode activity;
   b. each partial body (400, 401) and each connecting element (410) is formed of the active electrode material (E), and
   c. each connecting element (410) has a smaller cross-sectional area perpendicular to the longitudinal axis (L) than its adjacent partial bodies (400, 401), whereby the cavity (110) is:
      (1) formed between the adjacent partial bodies (400, 401) and adjacent the connecting element (410), and
      (2) configured to ease mechanical separation of the adjacent partial bodies (400, 401) by severing the connecting element (410).

8. The electrode element (1) of claim 7 wherein:
   a. the cavity (110) is within the electrode body (100), and
   b. the cavity (110), and the filler material (F) therein, are entirely surrounded by the active electrode material (E).

9. The electrode element (1) of claim 7 further including an implantable electrotherapeutic device having the capacitor (200) therein.

10. The electrode element (1) of claim 7 wherein the cavity (110) extends along:
    a. an elongated path extending between edges of the electrode body (100), and
    b. a major portion of a distance between the edges of the electrode body (100).

11. The electrode element (1) of claim 7 defining an anode of the capacitor (200).

* * * * *